United States Patent
Wei et al.

(10) Patent No.: US 7,879,093 B2
(45) Date of Patent: Feb. 1, 2011

(54) ELECTROSPUN APATITE/POLYMER NANO-COMPOSITE SCAFFOLDS

(75) Inventors: Mei Wei, Coventry, CT (US); Fei Peng, Willington, CT (US); Zhi-kang Xu, Hangzhou (CN)

(73) Assignee: University of Connecticut, Farmington, CT (US)

( * ) Notice: Subject to any disclaimer, the term of this patent is extended or adjusted under 35 U.S.C. 154(b) by 209 days.

(21) Appl. No.: 12/055,865

(22) Filed: Mar. 26, 2008

(65) Prior Publication Data

US 2008/0292839 A1  Nov. 27, 2008

Related U.S. Application Data

(60) Provisional application No. 60/907,207, filed on Mar. 26, 2007.

(51) Int. Cl.
*A61F 2/02*  (2006.01)
(52) U.S. Cl. .............. 623/11.11; 623/16.11; 623/23.51; 424/422; 424/423; 428/372; 428/370
(58) Field of Classification Search ................. 428/372; 424/423, 422; 623/23.74, 11.11, 16.11, 23.51
See application file for complete search history.

(56) References Cited

U.S. PATENT DOCUMENTS

| | | | |
|---|---|---|---|
| 4,629,464 A | 12/1986 | Takata et al. | |
| 5,084,051 A * | 1/1992 | Tormala et al. | 606/77 |
| 7,758,882 B2 * | 7/2010 | Roeder et al. | 424/426 |
| 2003/0031698 A1 * | 2/2003 | Roeder et al. | 424/423 |
| 2004/0037813 A1 | 2/2004 | Simpson et al. | |
| 2005/0142162 A1 * | 6/2005 | Hunter et al. | 424/423 |
| 2005/0147643 A1 | 7/2005 | Hunter et al. | |
| 2005/0255779 A1 * | 11/2005 | Mizutani et al. | 442/411 |
| 2006/0067969 A1 | 3/2006 | Lu et al. | 424/423 |
| 2006/0199876 A1 | 9/2006 | Troczynski et al. | |
| 2006/0204539 A1 | 9/2006 | Atala et al. | 424/423 |
| 2006/0257377 A1 | 11/2006 | Atala et al. | 424/93.7 |
| 2007/0041952 A1 * | 2/2007 | Guilak et al. | 424/93.7 |
| 2007/0141333 A1 * | 6/2007 | Shastri et al. | 428/375 |
| 2007/0255422 A1 * | 11/2007 | Wei et al. | 623/23.51 |
| 2008/0112998 A1 * | 5/2008 | Wang | 424/423 |

(Continued)

FOREIGN PATENT DOCUMENTS

WO   WO 2006/036130 A1   4/2006

(Continued)

OTHER PUBLICATIONS

"Computation Capabilities of Artificial Neural Networks," *Fundamentals of Artificial Neural Networks*, M.H. Hassoun, Cambridge, Massachussetts, 1995, Chapter 2.

(Continued)

*Primary Examiner*—N. Edwards
(74) *Attorney, Agent, or Firm*—Baker Hostetler LLP

(57) ABSTRACT

An artificial bone composite structure is provided. This structure includes a fibrous matrix that itself includes a plurality of fibers. Also, the structure includes a plurality of hydroxyapatite (HA) particles. These particles are dispersed within the fibrous matrix. Also, the HA particles have controlled size and aspect ratios and are aligned along long axes of the fibers. In some instances, the fibers include poly-(L-lactic acid) (PLLA).

13 Claims, 10 Drawing Sheets

U.S. PATENT DOCUMENTS

2008/0220054 A1* 9/2008 Shastri et al. ............... 424/443

FOREIGN PATENT DOCUMENTS

WO    WO 2006/138718 A2    12/2006

OTHER PUBLICATIONS

"Deagglomeration of HA During the Precipitation Synthesis," F. Xiao, et al., *Journal of Materials Science* 40 (2005) 5439-5442.

"Design and Analysis of Tissue Engineering Scaffolds that Mimic Soft Tissue Mechanical Anisotropy," T. Courtney, et al., *Biomaterials* 27 (2006) 3631-3638.

"Effect of Ball Milling on the Processing of Bone Substitutes with Calcium Phosphate Powders," A. Bignon, et al., *Journal of Biomedical Materials Research*, vol. 63, pp. 619-626 (2002).

"Electrospinning of Collagen Nanofibers," J.A. Matthews, et al., *Biomacromolecules* 2002, 3, 232-238.

"Engineered Cellular Response to Scaffold Architecture in a Rabbit Trephine Defect," J.L. Simmons, et al., *Journal of Biomedical Materials Research*, vol. 66A, pp. 275-282 (2003).

"Fluid Flow Increases Mineralized Matrix Deposition in 3D Perfusion Culture of Marrow Stromal Ostoblasts in a Dose-Dependant Manner," G.N. Bancroft, et al., PNAS, Oct. 1, 2002, vol. 99, No. 20, pp. 12600-12605.

"In Vitro Analysis of Biodegradable Polymer Blend/Hydroxyapatite Composites for Bone Tissue Engineering," K.G. Marra, et al., *Journal of Biomedical Materials Research*, vol. 47, pp. 324-335 (1999).

"In Vitro Cytotoxicity and In Vivo Biocompatibility of Poly(Propylene Fumarate-*Co*-Ethylene Glycol) Hydrogels," L.J. Suggs, et al., *Journal of Biomedical Materials Research*, vol. 46, pp. 22-32 (1999).

"The Manufacturing Techniques of Various Drug Loaded Biodegradable Poly(Lactide-*Co*-Glycolide) (PLGA) Devices," R.A. Jain, *Biomaterials* 21 (2000) 2475-2490.

"Osteointegration of Hydroxyapatite-Titanium Implants Coated with Nonglycosylated Recombinant Human Bone Morphogenetic Protein-2 (BMP-2) in Aged Sheep," A. Sachse, et al., *Bone* 37 (2005) 699-710.

"Porous Hydroxyapatite and Tricalcium Phosphate Cylinders with Two Different Pore Size Ranges Implanted in the Cancellous Bone of Rabbits," P.S. Eggli, M.D., et al., *Clinical Orthopaedics and Related Research*, No. 232, Jul. 1988, pp. 127-138.

"Preparation of Antibacterial Silver-Doped Silica Glass Microspheres," M. Kawashita, et al., *Journal of Biomedical Materials Research*, vol. 66A, pp. 266-274 (2003).

"Processing of Fine Hydroxyapatite Powders via an Inverse Microemulsion Route," G.K. Lim, et al., *Materials Letters* 28 (1996) 431-436.

"Processing of Hydroxyapatite via Microemulsion and Emulsion Routes," G.K. Lim, et al., *Biomaterials* 18 (1997) 1433-1439.

"Revised Simulated Body Fluid," H.M. Kim, et al., *Key Engineering Materials*, vols. 192-195, 2001, pp. 47-50.

"Scaffolds in Tissue Engineering Bone and Cartilage," D.W. Hutmacher, *Biomaterials* 21 (2000) 2529-2543.

"Spatial Control of Protein within Biomimetically Nucleated Mineral," L.N. Luong, et al., *Biomaterials* 27 (2006) 1175-1186.

"Studies on the Formation of Biomimetic Apatite Layers on 3D-Printed Biodegradable Polymeric Scaffolds: Effect of Different Dynamic Coating Routes," A.L. Oliveira, et al., 2006 Annual Meeting of the Society from Biomaterials, Pittsburgh, PA, USA, May 2006.

"Tape Casting of Porous Hydroxyapatite Ceramics," E. Roncari, et al., *Journal of Materials Science Letters*, 19 (2000) 33-35.

"Tensile Test of a Single Nanofiber Using an Atomic Force Microscope Tip," E.P.S. Tan, et al., *Applied Physics Letters*, 86, 073115 (2005), 1-3.

"Ultrasonic Dispersion of Ceramic Powders," E. Jorge, et al., *Journal of American Ceramic Society*, 73 (8), 2252-2254, (1990).

\* cited by examiner

| Sample Symbol | HA wt% | Fibrous Assembly | Young's Modulus/ MPa | Tensile Stress/ MPa | Tensile Strain/ % |
|---|---|---|---|---|---|
| Upsidedown triangle | 0 | Not aligned | 65.9 ± 4.3 | 2.9 ± 0.1 | 33.5 ± 5.0 |
| Triangle | 0 | Aligned | 314.0±26.5 | 16.5±1.6 | 25.8 ± 3.5 |
| Circle | 20 | Not aligned | 122.7±12.0 | 4.6 ± 0.2 | 7.6 ± 1.4 |
| Square | 20 | Aligned | 762.3±63.7 | 28.9±0.7 | 7.4 ± 1.1 |

ELECTROSPUN APATITE/POLYMER NANO-COMPOSITE SCAFFOLDS

CROSS-REFERENCE TO RELATED APPLICATIONS

This application claims priority to provisional U.S. patent application entitled, "Electrospun Apatite/Polymer Nano-Composite Scaffolds," filed Mar. 26, 2007, having Ser. No. 60/907,207, now pending, the disclosure of which is hereby incorporated by reference in its entirety.

FIELD OF THE INVENTION

The present invention relates generally to composite materials. The present invention also relates generally to methods of making composite materials.

BACKGROUND OF THE INVENTION

One prominent area of current scientific research in the medical field is focused upon artificially replicating human bones and other types of tissues. One of the goals of such research is to provide surgeons with artificially fabricated materials that may then be incorporated into a human patient during surgery.

Currently, some surgeons remove bone or tissues from one portion of a patient's body and reattach the bone or tissues in another portion of the patient's body. For example, during spinal surgery, bone from the hip is sometimes removed and incorporated into the spine. Some other surgeons are forced to incorporate metal components (e.g., metal rods and/or plates) in portions of a patient's body where natural bone has been shattered or has deteriorated.

Structurally, natural bone is a composite material that includes hydroxyapatite (HA) and fibrous collagen. In natural bone, the HA crystals are embedded within the collagen fiber matrix and are aligned along the long axis of fibers.

Currently, no method exists for artificially replicating the exact structure of natural bone. Even the most advanced methods for artificially replicate natural bone structure have at least been unsuccessful in aligning HA crystals in a manner analogous to the alignment in natural bone. As such, artificially generated bone does not have the same mechanical/biological/chemical properties as naturally occurring bone.

SUMMARY OF THE INVENTION

According to certain embodiments of the present invention, an apatite/fibrous polymer nano-composite scaffold has been fabricated using electrospinning. Electrospinning is a convenient and versatile fabrication technique which produces fibers with diameters from approximately 50 nm to several micrometers. According to certain embodiments of the present invention, the structure generated by electrospinning is highly porous with interconnected pores. This fibrous structure typically resembles the architecture of an extracellular matrix (ECM). These fibrous structures may be used as artificial bone composite. Furthermore, these fibrous structures may be used with other tissues based on biocompatibility, mechanical properties, and cell attachment and growth of the fibrous structures and the tissues.

According to certain other embodiments of the present invention, HA particles with sizes ranging from approximately 10 nm to approximately 10 μm and having an average aspect ratio up to approximately 50 are synthesized. The HA particles are well dispersed in the spinning dope and co-electrospun with polymer nanofibers. The HA/PLLA nano-composite fibrous scaffold can be fabricated with HA particles homogenously distributed within the PLLA nanofibers.

According to still other embodiments of the present invention, up to approximately 20 wt % of HA nanoparticles is incorporated into the PLLA nanofibers. These nanoparticles are well aligned along the long axes of the polymer fibers. Such obtained microstructure closely mimics the micro-arrangement of the inorganic/organic components in the ECM of natural bone. Such fabricated scaffolds have desirable mechanical properties and good cell signaling properties. At least in view of the above, such scaffolds are suitable for loading cells and biological active agents. It should also be noted that incorporation of more than 20 wt % HA nanoparticles is also within the scope of certain embodiments of the present invention.

It is desirable to fabricate bone graft materials mimicking the structural, mechanical, and biological behavior of natural bone. This need is met, to a great extent, by certain embodiments of the present invention, particularly those wherein a structure is provided that includes a scaffold and highly crystallized, well-dispersed HA nanoparticles. In this structure, the HA nanoparticles have controllable aspect ratios within the range of approximately 5 and approximately 50.

According to other embodiments of the present invention, a structure is provided that includes a fibrous matrix that itself includes a plurality of fibers. The structure also includes a plurality of hydroxyapatite (HA) particles dispersed within the fibrous matrix, wherein the HA particles are substantially aligned along long axes of the plurality of fibers.

According to yet other embodiments of the present invention, a method of forming a structure is provided. The method includes adding hydroxyapatite (HA) particles to a poly-(L-lactic acid) (PLLA) solution to form a mixture and forming an HA/PLLA fiber by electrospinning the mixture.

According to still other embodiments of the present invention, a structure is provided that includes a fibrous matrix including a plurality of fibers. The structure also includes a plurality of hydroxyapatite (HA) particles dispersed within the fibrous matrix, wherein the HA particles are substantially aligned along long axes of the plurality of fibers, wherein the structure is manufactured by adding the HA particles to a poly-(L-lactic acid) (PLLA) solution to form a mixture and by forming HA/PLLA fibers by electrospinning the mixture to form the fibrous matrix.

There has thus been outlined, rather broadly, certain embodiments of the invention in order that the detailed description thereof may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 1(a) illustrates a field emission scanning electron microscope (FESEM) image of electrospun PLLA nanofibers, FIG. 1(b) illustrates an FESEM image of HA/PLLA (20:80 w/w) composite nanofibers, and FIG. 1(c) illustrates a transmission electron microscope (TEM) image of HA/PLLA/HA (20:80 w/w) composite nanofibers.

FIG. 2(a) illustrates the effect of varying PLLA concentration in the electrospinning dope. FIG. 2(b) illustrates the effect of varying the amount of HA incorporation (wt %) in the composite fibers. FIG. 2(c) illustrates the effect of varying power voltage. FIG. 2(d) illustrates the effect of varying the injection rate. FIG. 2(e) illustrates the effect of varying the spinneret inner diameter. FIG. 2(f) illustrates the effect of varying the distance between the spinneret tip and the collector on the diameter of the electrospun nanofibers.

FIG. 3(a) is a TEM image of polyethylene glycol (PEG)-core-PLLA-shell nanofibers. FIG. 3(b) is an FESEM image of highly aligned PLLA nano fibers. FIG. 3(c) is an FESEM image of highly porous PLLA nano fibers.

FIG. 4(a) illustrates typical stress v. strain curves for HA/PLLA electrospun scaffolds with an averaged fiber diameters equal to 110±15 nm. FIG. 4(b) illustrates Young's moduli (E, hatched bars) and tensile stresses (solid bars) of HA/PLLA electrospun scaffolds with averaged fiber diameters equal to 110±15 nm. FIG. 4(c) illustrates Young's moduli (E) and tensile stresses of different component HA/PLLA electrospun scaffolds with averaged fiber diameters equal to 170±25 nm.

FIG. 5(a) illustrates the stress vs. strain curves for electrospun fibrous scaffolds with different compositions and fibrous assemblies.

FIG. 6(a) illustrates the average diameters and standard variations for fibers electrospun from different PLLA concentrations. The concentration used in FIG. 6(b) was PLLA=4.0 wt %. The concentration used in FIG. 6(c) was PLLA=6.0 wt %. The concentration used in FIG. 6(d) was PLLA=8.0 wt %. The concentration used in FIG. 6(e) was PLLA=10.0 wt %. FIG. 6(b)-(e) were all taken at a magnification of ×20,000.

in FIG. 6(a), via a metathesis reaction at 70° C. in FIG. 7(b), via a metathesis reaction at 95° C. in FIG. 7(c), and via a urea decomposition at 95° C. in FIG. 7(d). One of skill in the art will recognize that HA particles with different sizes and aspect ratios are evenly distributed within the illustrated polymer nanofibers. Also, the composites illustrated in FIGS. 7(a)-(d) demonstrate a good orientation along the long axis of the PLA nanofibers. The HA content in these composites are 20 wt %.

DETAILED DESCRIPTION

Figure 1A:
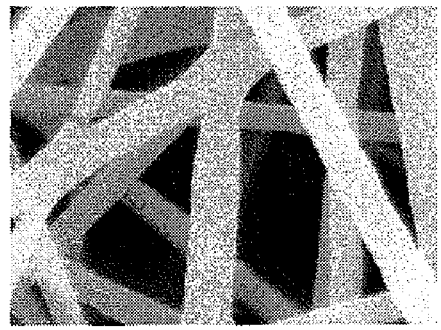
FIGS. 1(a)-(c) illustrate morphologies of electrospun PLLA and HA/PLLA composite nanofibers. More specifically.

The invention will now be described with reference to the drawing figures, in which like reference numerals refer to like parts throughout. According to certain embodiments of the present invention, HA/PLLA composite scaffolds are electrospun. However, it should be noted that other composite systems using materials other than HA and PLLA are also within the scope of certain embodiments of the present invention. For example, collagen, hyaluronans, fibrin, chitosan, alginate, other animal- or plant-derived polymers, PLA, PCL, PGA, other synthetic and natural polymers, polyesters, polyethers, polycarbonates, polyamines, polyamides, and their co-polymers and combinations may be used. Also, for example, carbonated HA, and other calcium phosphates (e.g., ion-substituted apatites, such as carbonate hydroxyapatite, fluorinated hydroxyapatite, chlorinated hydroxyapatite, silicon-containing hydroxyapatite, magnesium-containing hydroxyapatite and other ion substituted HA, tricalcium phosphate, tetracalcium phosphate, monetite, dicalcium phosphate, dicalcium phosphate dihydrate, octacalcium phosphate, or calcium sulfate) may also be used. The effect of the processing parameters on fiber diameter has been carefully studied and the polymer molecular weight and dope concentration greatly affected fiber diameters ranging from 50 nm to 500 nm.

In order to fabricate the above-discussed scaffolds, HA particles were added to a PLLA solution to fabricate an HA/PLLA composite. Also, the amount of HA in the PLLA solution was adjusted by varying the HA to PLLA feeding ratio in the spin-dope.

According to certain embodiments of the present invention, up to approximately 20 wt % of HA is incorporated into PLLA nanofibers. These HA particles are typically well aligned along the long axis of the polymer fibers. The size of the HA particles have an average width of at least 10 nm and an average length ranged from approximately 10 nm to approximately 10 µm, with an average aspect ratio up to approximately 50. The particles, according to certain embodiments of the present invention, were homogenously distributed within the PLLA nanofibers after electrospinning. The resultant microstructure closely mimicked the arrangement of the inorganic/organic components in ECM of natural bone. Compared to the fibrous scaffold fabricated with pure PLLA, the HA/PLLA scaffold has improved mechanical properties and biocompatibility.

Figure 1B:
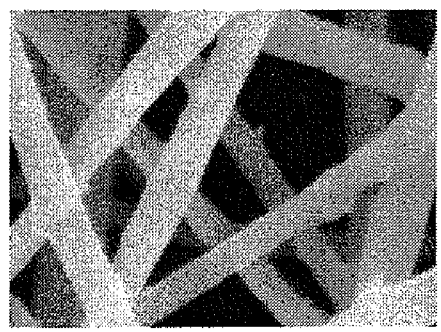
Figure 1C:
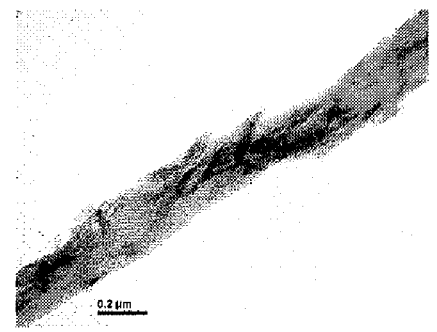
Figure 2A:
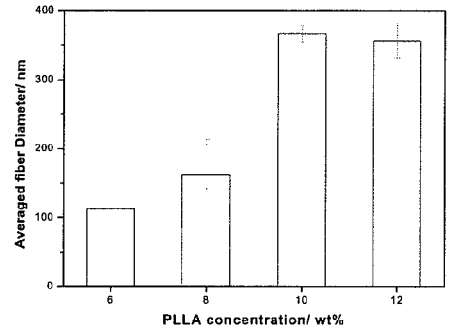
FIGS. 2(a)-(f) illustrate the effect of varying various electrospinning parameters.
Figure 2B:
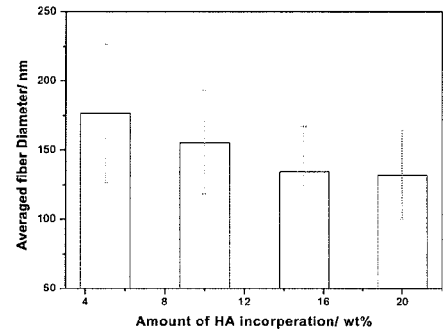
Figure 2C:
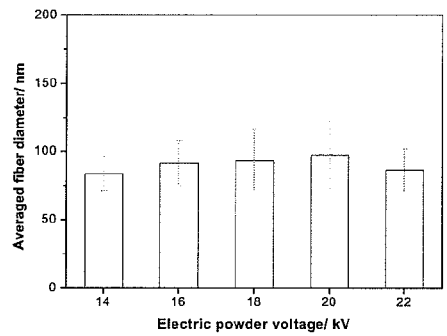
Figure 2D:
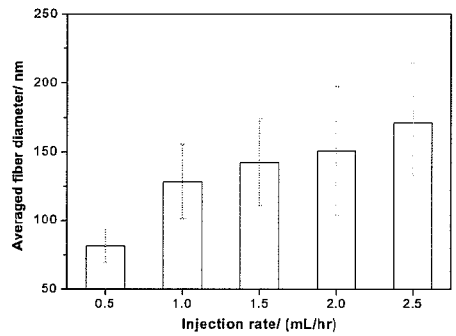
Figure 2E:
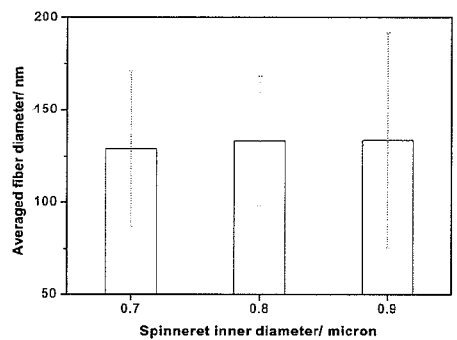
Figure 2F:
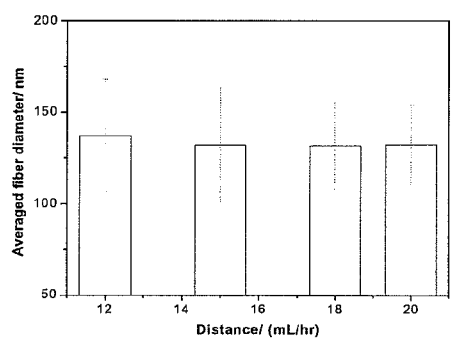

As illustrated in FIGS. 1(a)-(c), HA particles with lengths between 100 and 200 nm and aspect ratios between 7 and 10 were evenly distributed within HA/PLLA fiber bodies. These particles also demonstrated a good orientation along the long axes of the PLLA nanofibers.

The effects of altering the electrospinning processing parameters on the diameter of HA/PLLA composite fibers were studied in FIG. 2. As illustrated, varying the polymer concentration of the electrospinning dope and varying the HA/PLLA weight ratio have the most obvious influences on the diameter. As illustrated in FIG. 2(a), the diameter of composite nanofibers increase with the PLLA concentration in the spinning dope, which indicates that a high PLLA concentration dope has higher surface tension and was more difficult to be spun into finer fibers during the fiber spinning process. FIG. 2(b) illustrates that composite fiber diameter decreases with increasing HA weight ratio. This is likely explained by the fact that higher amounts of HA in a composite decreases the viscosity of the electrospinning dope and the surface tension thereof as well.

Figure 3A:
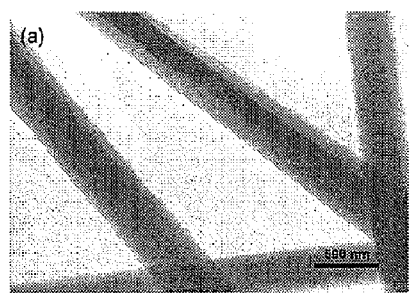
FIGS. 3(a)-(c) illustrate functionalized PLLA fibers.
Figure 3B:
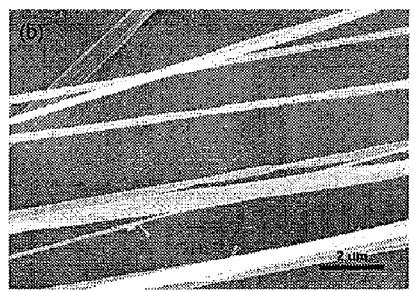
Figure 3C:
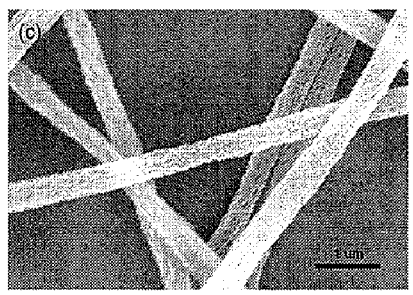

As illustrated in FIG. 3, several modified electrospinning techniques for fabricating functionalized nanofibrous scaffolds have been implemented according to various embodiments of the present invention. First, a PEG/PLLA core-shell structure has been co-electrospun into a fibrous composite scaffold using co-axial dual spinnerets, as shown in FIG. 3(a). Second, highly aligned nanofibers were fabricated using a rotating drum as the collector, as illustrated in FIG. 3(b). Scaffolds prepared in this manner have good orientation and improved mechanical strength along the long axes of the fibers. Third, nanofibers with a porous surface have been electrospun using a mixture of $CH_2Cl_2$ (DCM) and DMF (DCM/DMF=6/1 (v/v)) as a solvent, as illustrated in FIG. 3(c).

As illustrated in FIG. 3, the porosity and pore size of fibers according to certain embodiments of the present invention can be adjusted by altering the solvent used and dope concentration. The porous surface of the fibers can be used, for example, for controlled delivery of growth factors. Moreover, the porous surface will also enhance the bonding strength between the polymer fiber and a biomimetic apatite coating, such as the one illustrated in FIG. 8(b). The porous surface may also act as a nucleation site for apatite further growth.

Figure 4:
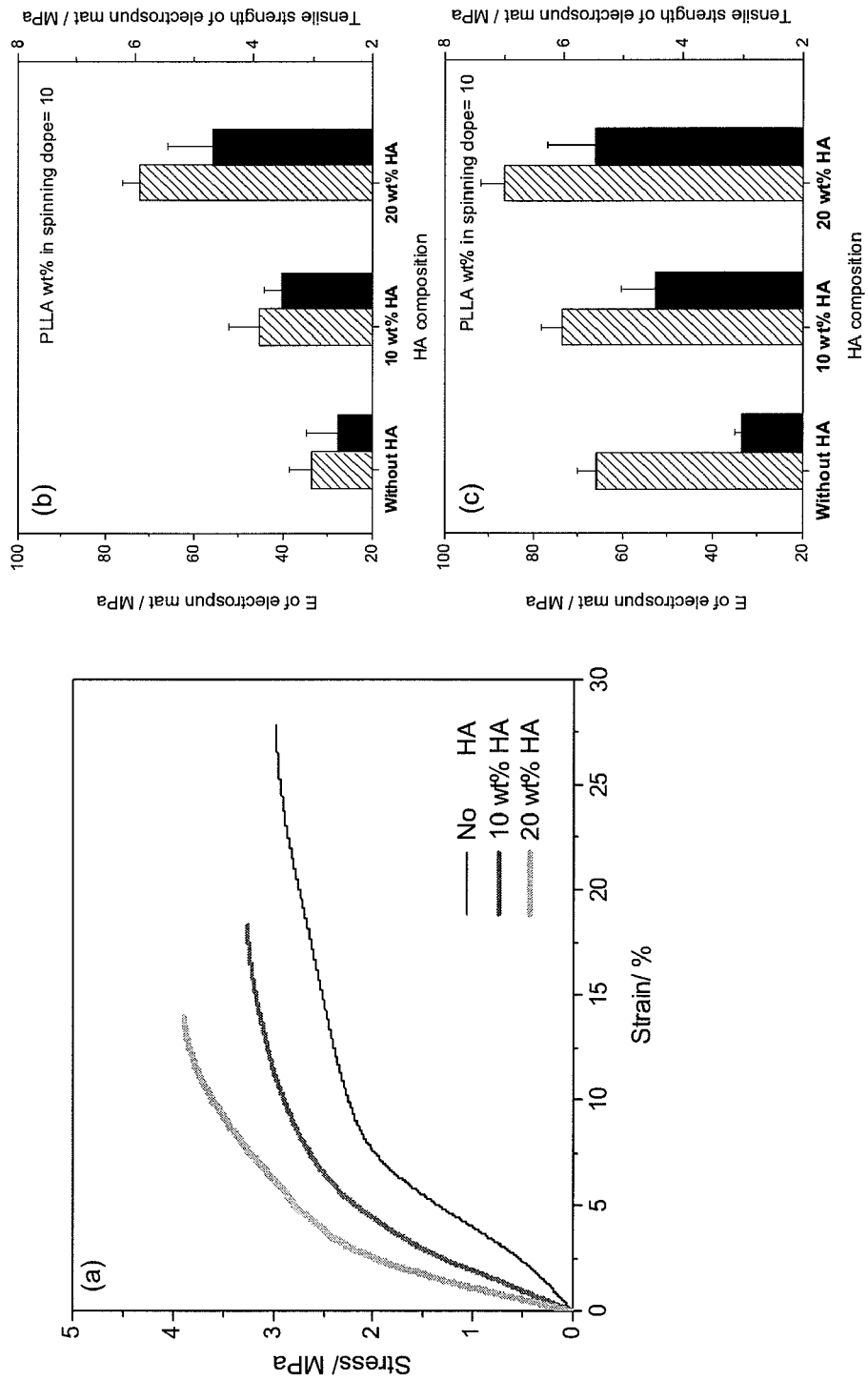
FIGS. 4(a)-(c) illustrate the mechanical properties of electrospun PLLA and HA/PLLA scaffolds.

FIG. 4 compares mechanical properties of various electrospun composite fibers with different HA incorporation ratios. One of skill in the art will recognize, upon analyzing FIGS. 4(a)-(c), that both the Young's moduli and tensile stresses of the electrospun mats increased continuously as the HA incorporation ratio increased. This can be explained by the fact that HA, when well dispersed and aligned along fiber long axes, plays a substantial role in reinforcing the composite fibrous mat. Comparisons between the data included in FIG. 4(b) and FIG. 4(c) also demonstrates that fibrous mats with thicker composite nanofibers present more desirable mechanical properties.

Figures 5A, 5B:
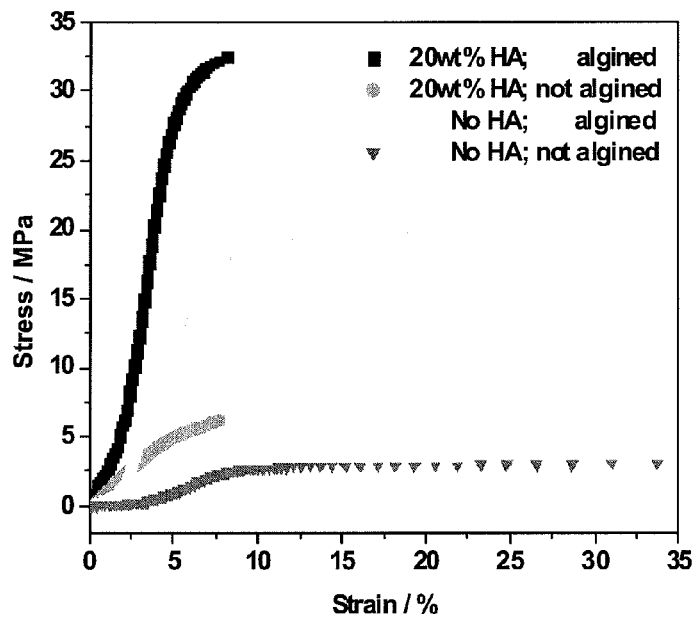
FIGS. 5(a) and (b) illustrate the mechanical properties of electrospun fibrous scaffolds with different compositions and fibrous assemblies.
FIG. 5(b) illustrates the tensile test results for electrospun fibrous scaffolds with different compositions and fibrous assemblies.
Figure 6:
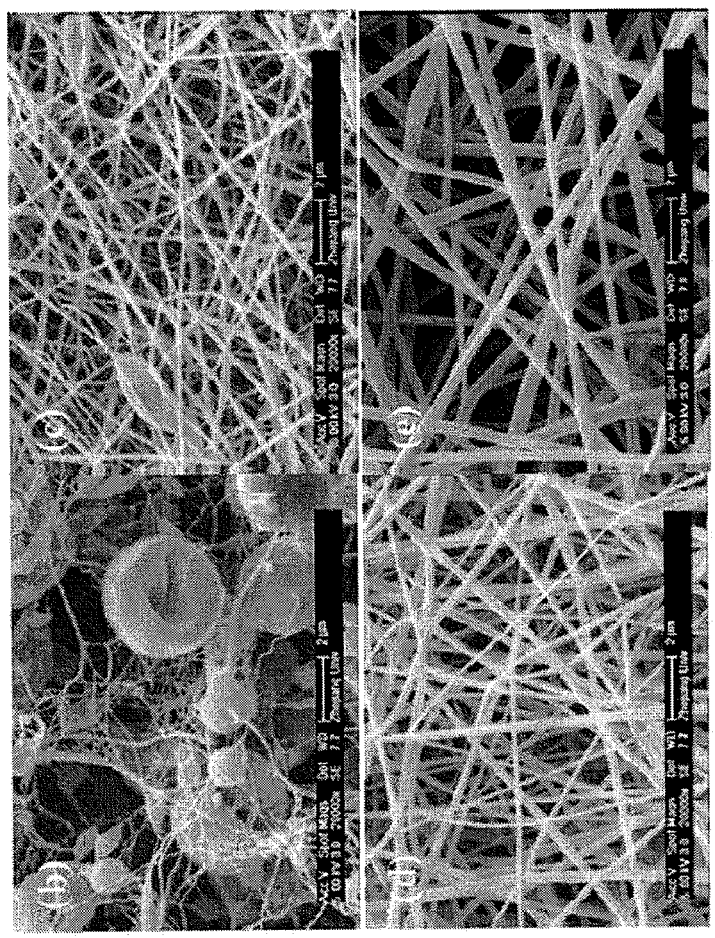
FIGS. 6(a)-(e) illustrate PLLA nanofibers obtained from electrospinning according to certain embodiments of the present invention.
Figure 6:
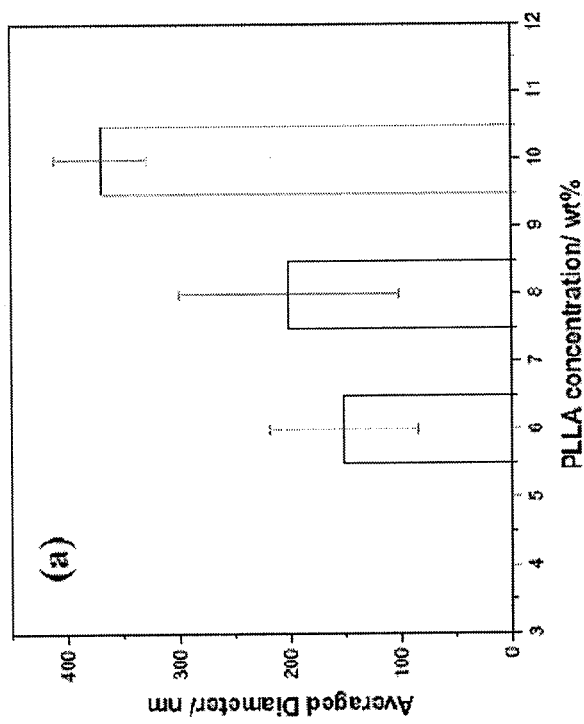
Figure 7:
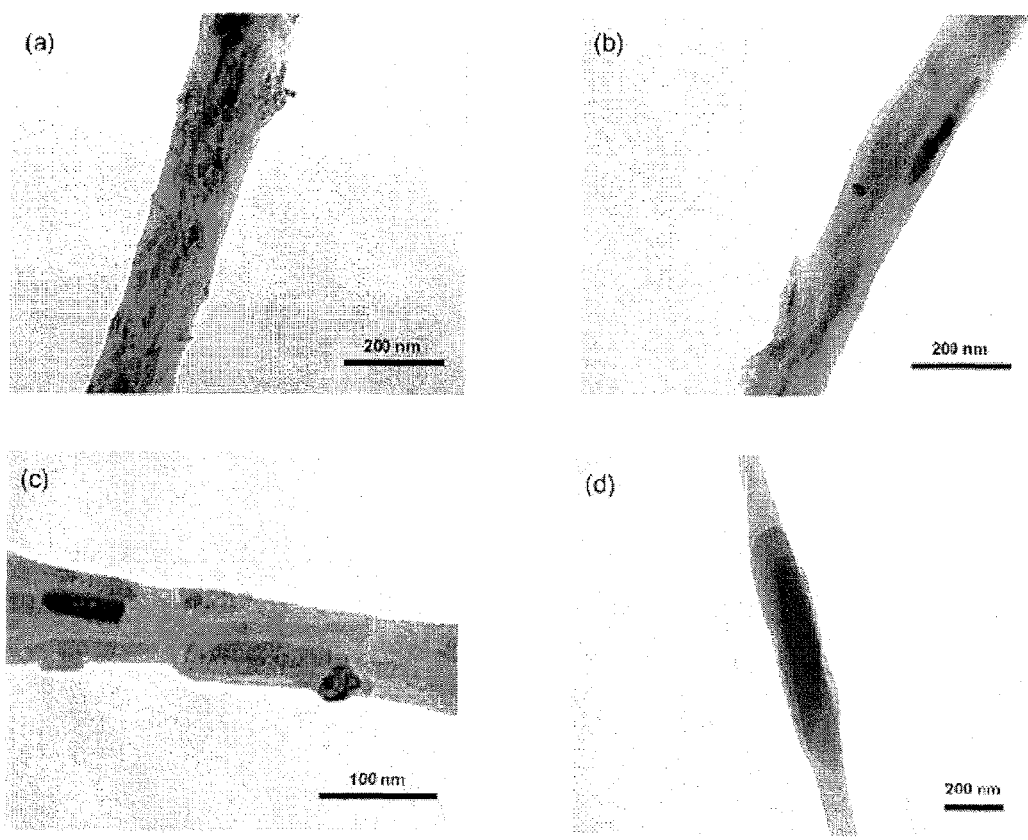
FIGS. 7(a)-(d) illustrate electrospun HA/PLLA composites. The HA particles in the composite were synthesized via a metathesis reaction at 100° C.

FIG. 5(a)-(b) illustrates the mechanical properties of electrospun PLLA-based scaffolds using tensile test. One of skill in the art will recognize that both the alignment of the scaffold assembly and the incorporation of nano-size, needle-shape HA particles into the nano-fibers significantly improved the elastic modulus of the composite scaffold. The scaffold with HA particles are much stiffer than those without HA particles, and the elastic modulus of the former is more than two times as high as that of the later. It is also shown that, the HA nanoparticles inhibit un-folding and orientation of PLLA molecular chains within spun fibers during tensile testing, i.e. cold drawing of the scaffold, and decrease the toughness of the composite scaffolds by decreasing their elongation at break.

According to certain embodiments of the presentation, the elastic modulus of the scaffolds with aligned assembly is four to five times higher than those with random fibrous assembly. Moreover, the pure PLLA scaffold with aligned assembly has much higher toughness but lower elongation at break than those with a random assembly. In the case of HA/PLLA scaffolds, such difference is not as significant as that of the pure PLLA scaffolds.

Figure 8:
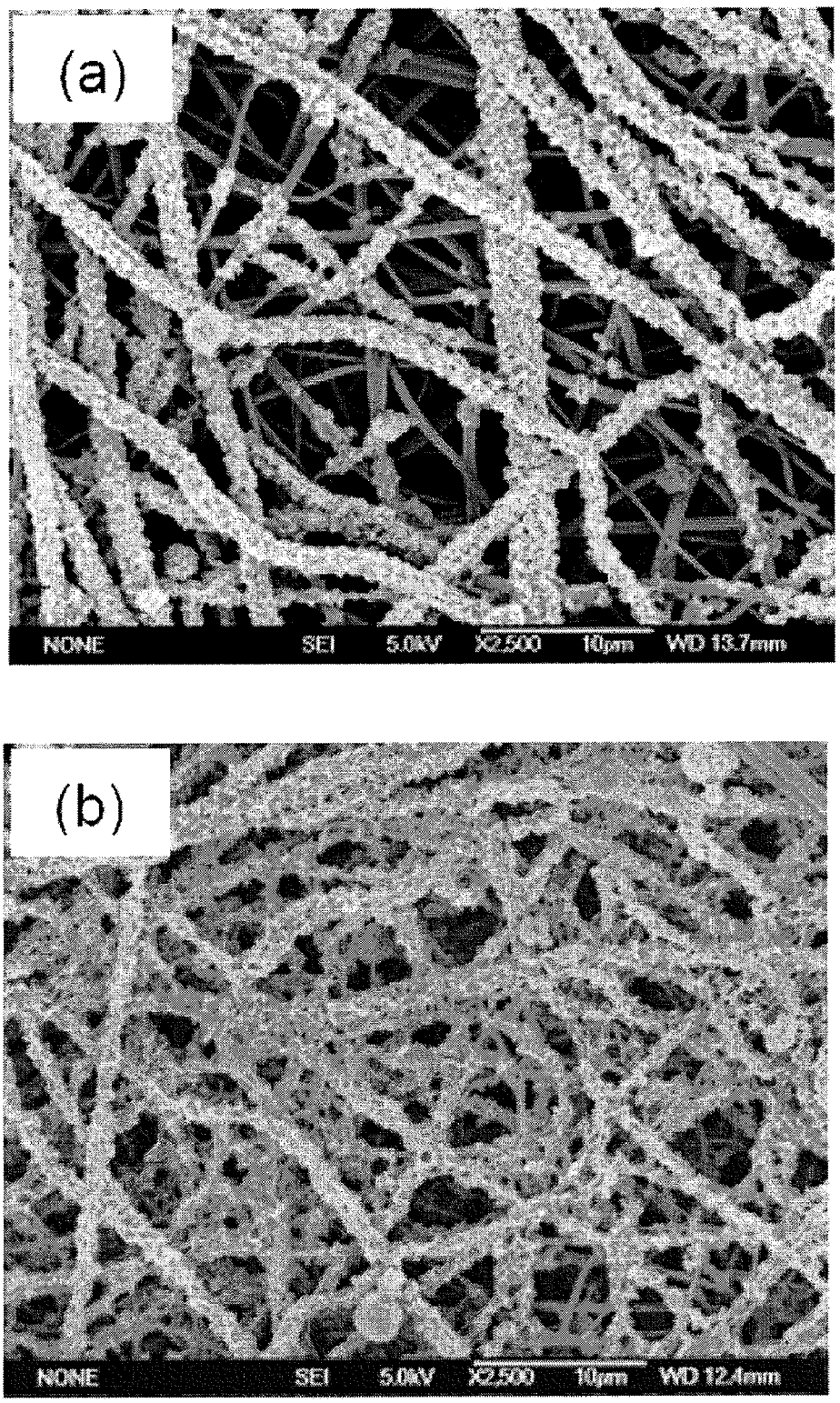
FIGS. 8(a)-(b) illustrate thin layers of a biomimetic apatite coating on the surface of PLLA and HA/PLLA scaffolds, respectively.

According to certain embodiments of the present invention, a homogenous apatite coating layer can also be formed on the surface of both PLLA and HA/PLLA scaffolds, as shown in FIGS. 8(a)-(b). The thickness of the coating is a few micrometers, which was obtained after approximately 4 hr of immersion in a modified simulated body fluid (m-SBF). The thickness of the coating can be adjusted by varying the Ca and P ion concentrations in SBF, sample immersion time, and pH of the solution.

According to certain embodiments of the present invention, maintaining the immersion time short is important in order to maintain the integrity of the polymer fibers. According to some of these embodiments, some polymer fibers absorb water, which leads to the reduction of their mechanical properties. Nevertheless, the thickness of the coating can be adjusted by varying the coating conditions such as, the m-SBF pH, immersion time, and calcium and phosphorous concentrations.

Figure 9:
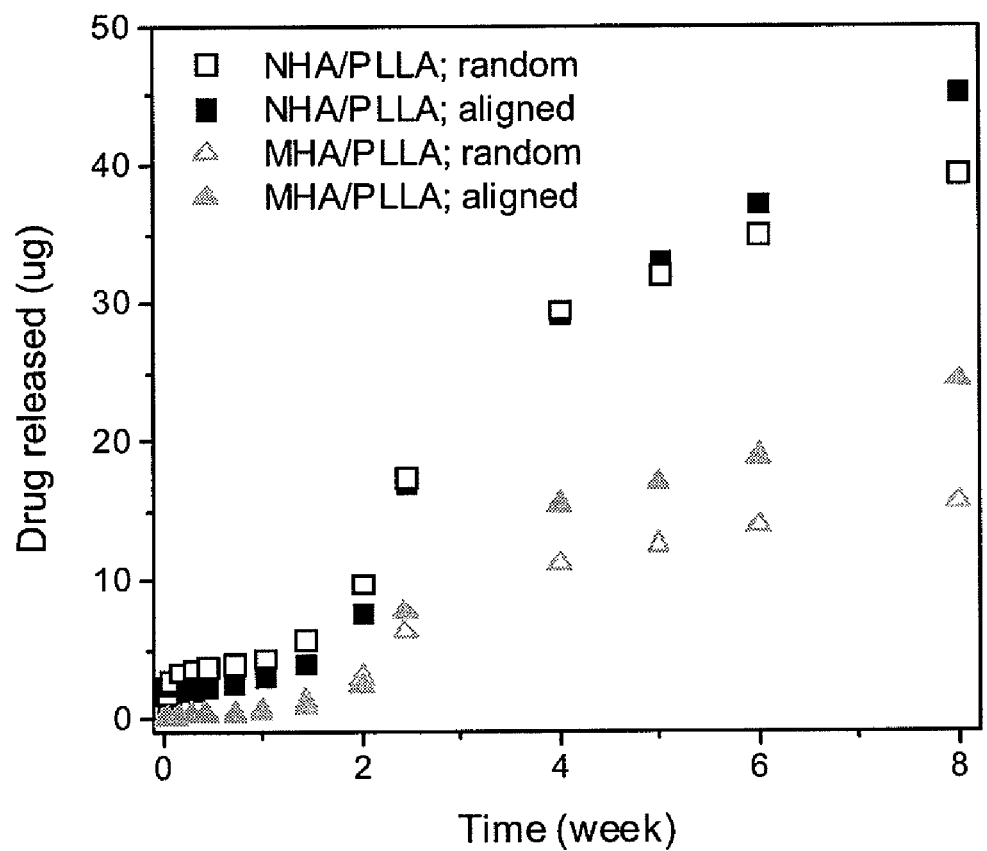
FIG. 9 illustrates in vitro release of FITC-BSA from electrospun HA/PLLA fibrous scaffold with needle-shape HA particles either at nano- (NHA) or microsize (MHA) and with either random or aligned fibrous assembly.

According to certain embodiments of the present invention, fluorescein isothiocyanate labeled bovine serum albumin (FITC-BSA) was incorporated into the biomimetic apatite coating formed on the surfaces of the scaffold, to study the drug release behaviors of the electrospun scaffolds. The drug release profiles of the electrospun HA/PLLA fibrous scaffolds are shown in FIG. 9. The release of FITC-BSA from the biomimetic coating on the scaffold was studied for a time period of 8 weeks. Sustained release profiles have been observed for all scaffolds. The scaffolds with nano-size HA particles (NHA) showed faster release profiles than those incorporated with micro-size HA particles (MHA). Also, a slightly faster release has been observed for the scaffolds with an aligned assembly than those with a random assembly. According to certain embodiments of the present invention, the biomimetic coating formed on the electrospun scaffold can be an effective carrier for sustained release of proteins and/or drugs.

Figure 10:
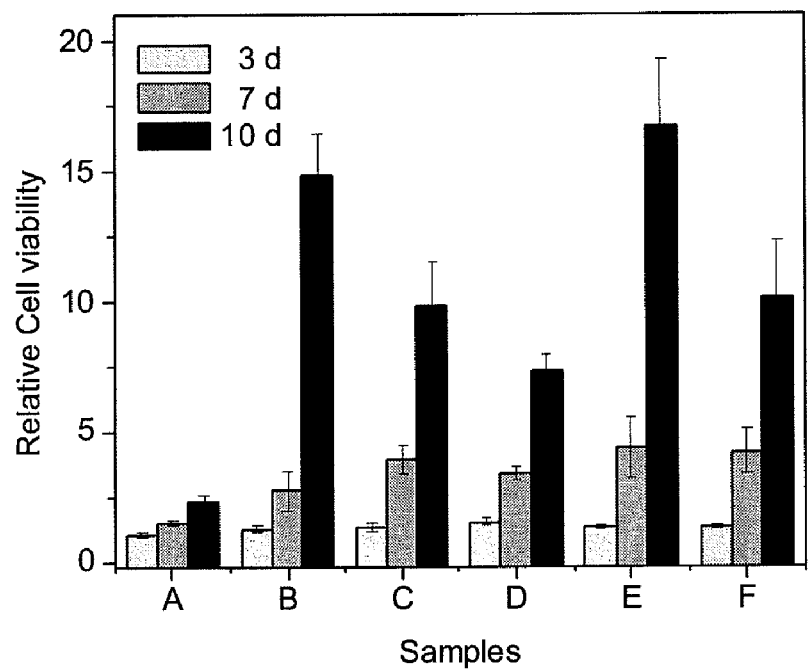
FIG. 10 illustrates relative cell viability on different scaffolds after being cultured for 3, 7, and 10 days. (Sample A) PLLA scaffold with random assembly, (Sample B) micrometer-size HA/PLLA scaffold with random assembly, (Sample C) nanometer-size HA/PLLA scaffold with random assembly, (Sample D) biomimetic apatite-coated nanometer-size HA/PLLA scaffold with random assembly, (Sample E) micrometer-size HA/PLLA scaffold with aligned assembly, and (Sample F) nanometer-size HA/PLLA scaffold with aligned assembly.

According to certain embodiments of the present invention, PLLA-based electrospun scaffolds with different HA particles were used for in vitro cell culture study. Rat osteosarcoma cell line ROS17/2.8 was used. FIG. 10 illustrates relative cell viability on different scaffolds. According to certain embodiments of the present invention, with the increase of the cell culture time, more cells were attached to the surface of the scaffold. Especially, more cells were found on the scaffolds incorporated with either nano- or micro-size HA particles than those on pure PLLA scaffold after 7 days of culture. After 10 days, such difference became much more significant.

Figure 11:
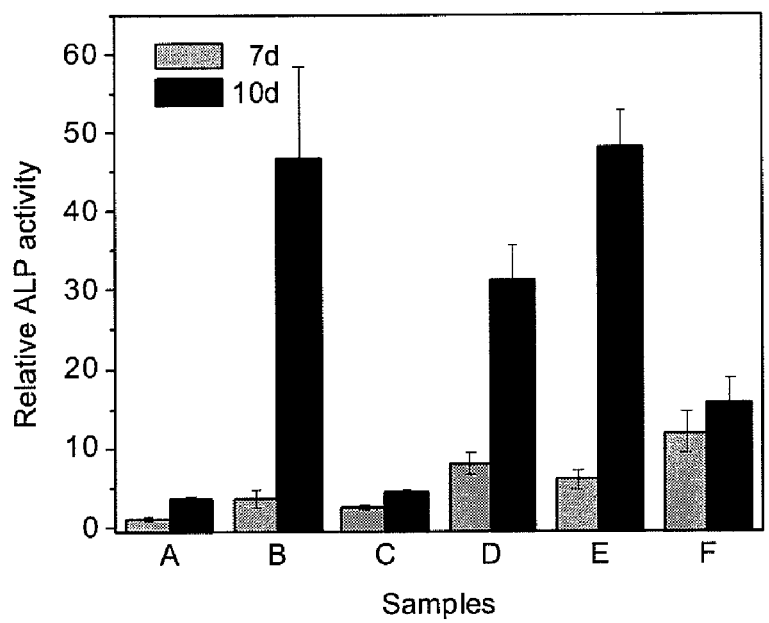
FIG. 11 illustrates relative alkaline phosphatase (ALP) activities on different scaffolds after being cultured for 7 and 10 days. (Sample A) PLLA scaffold with random assembly, (Sample B) micrometer-size HA/PLLA scaffold with random assembly, (Sample C) nanometer-size HA/PLLA scaffold with random assembly, (Sample D) biomimetic apatite-coated nanometer-size HA/PLLA scaffold with random assembly, (Sample E) micrometer-size HA/PLLA scaffold with aligned assembly, and (Sample F) nanometer-size HA/PLLA scaffold with aligned assembly.

According to certain embodiments of the present invention, the cell alkaline phosphatase (ALP) activities, an early marker of bone formation, on different scaffolds are shown in FIG. 11. According to certain embodiments of the present invention, after 10 days of culture, almost all the HA incorporated scaffolds showed significantly higher ALP activities than the control, pure PLLA scaffold. These results collectively suggested that hydroxyapatite has improved the biocompatibility and cell signaling properties of the scaffold, which could make the scaffold a better material for bone fracture repair.

According to certain embodiments of the present invention, a thicker apatite coating was obtained for the HA/PLLA scaffolds than the pure PLLA scaffolds with the same SBF soaking time. This may be explained by the fact that some of the HA particles loaded in the PLLA fibers position themselves on the surfaces of the fibers and act as nucleation sites for the apatite coating growth. Also, according to certain embodiments of the present invention, the coating grew more effectively on the top surface than the interior for both pure PLLA and HA/PLLA scaffold.

HA/PLLA composite fibrous scaffolds that include microscale pores throughout the body of the scaffold owing to electrospinning are also within the scope of the present invention. Such scaffolds, according to certain embodiments of the present invention, include nanometer-size pores on the surface of fibers in the scaffold owing to an evaporation process of highly volatile solvent. In such embodiments, nanoporous surfaces on composite fibers in the scaffold not only contribute to better bonding between a fiber substrate and an HA coating applied through a biomimetic coating method, but also induce fast degradation of the composite fibers.

According to certain embodiments of the present invention, in order to promote a more homogenous apatite coating throughout the scaffold, a pumping device is used to assist m-SBF penetrating into the scaffold or to create relatively large pores in the scaffold. Pores in the range of hundreds of micrometers, according to certain embodiments of the present invention, are desirable for both the invasion of blood vessels to provide the necessary nutrient supply to the transplanted cells and the bone formation.

Other embodiments of the present invention include HA/PLLA composite fibrous scaffolds that include at least one composite fiber surface and an HA coating on the composite fiber surface. According to some of these embodiments, the coating is formed by using a biomimetic coating method. Also, the obtained HA coating layer on the fiber surface will typically not only increase the HA component within the scaffold and contribute to improved mechanical properties of the scaffold, but will also increase the exposure of HA to the surrounding tissue during in vivo application. Such exposure can improve the biocompatibility as well as the osteoconductivity of the composite scaffold.

Also according to certain embodiments of the present invention, a HA/PLLA composite fibrous scaffold is provided that includes poly-lactic-co-glycolic acid (PLGA) microspheres incorporated among fibers. According to some of these embodiments, the size of the microspheres is controlled to be above 100 micrometers. This typically not only increases the mechanical properties of the fibrous scaffold but may also be used as a carrier for releasing one or more different drugs.

Using scaffolds such as the ones discussed above, a method of multi-drug delivery may be implemented. For example, two or more different drugs may be preloaded into different components of an electrospinning composite dope and PLGA microspheres to form a composite fibrous scaffold. Then, the drugs may be subsequently controllably released.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. An artificial composite structure, comprising:
a matrix having a plurality of fibers; and
a plurality of elongated hydroxyapatite (HA) particles dispersed within the matrix, wherein the elongated HA particles are substantially aligned along long axes of the plurality of fibers.

2. The structure of claim 1, wherein the plurality of fibers has an average diameter of between approximately 50 nm and several micrometers.

3. The structure of claim 1, wherein the HA particles have an average width of at least 10 nm and an average length ranged from approximately 10 nm to approximately 10 micrometers.

4. The structure of claim 1, wherein the plurality of fibers is selected from the group consisting of poly-(L-lactic acid) (PLLA), collagen, hyaluronans, fibrin, chitosan, alginate, animal-derived polymers, plant-derived polymers, PLA, PCL, PGA, synthetic polymers, natural polymers, polyesters, polyethers, polycarbonates, polyamines, polyamides, co-polymers, and combinations thereof.

5. The structure of claim 1, wherein up to 20 weight percent of elongated HA particles are incorporated into the matrix.

6. The structure of claim 1, wherein the elongated HA particles have aspect ratios between approximately 3 and approximately 50.

7. The structure of claim 1, wherein the plurality of fibers comprise a polyethylene glycol (PEG) core and a PLLA shell.

8. The structure of claim 1, further comprising an apatite coating layer on the matrix.

9. The structure of claim 1, further comprising: poly-lactic-co-glycolic acid (PLGA) microspheres incorporated among the plurality of fibers.

10. The structure of claim 1, wherein the elongated HA particles are distributed homogenously along the fibers.

11. A structure, comprising:
a matrix having a plurality of fibers; and
a plurality of needle-shaped hydroxyapatite (HA) particles dispersed within the matrix, wherein the HA particles are substantially aligned along long axes of the plurality of fibers, wherein the structure is formed by adding the HA particles to a poly(lactic acid) (PLA) solution to form a mixture and HA/PLA fibers are formed by electrospinning the mixture to form the matrix.

12. The structure of claim 11, wherein the HA particles have an average size of between approximately 10 nm and 10 micrometers.

13. The structure of claim 11, wherein the needle-shaped HA particles have aspect ratios between approximately 3 and approximately 50.

* * * * *